United States Patent
Singh

(10) Patent No.: US 10,061,998 B2
(45) Date of Patent: Aug. 28, 2018

(54) SYSTEM AND METHOD FOR SCHEDULING PLURALITY OF IMAGING TASKS IN A MEDICAL IMAGING SYSTEM

(71) Applicant: General Electric Company, Schenectady, NY (US)

(72) Inventor: Umesh Kumar Singh, Bangalore (IN)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 224 days.

(21) Appl. No.: 15/080,946

(22) Filed: Mar. 25, 2016

(65) Prior Publication Data

US 2016/0284083 A1    Sep. 29, 2016

(51) Int. Cl.
*G06K 9/00* (2006.01)
*G06K 9/32* (2006.01)
*G16H 40/20* (2018.01)

(52) U.S. Cl.
CPC .............. *G06K 9/32* (2013.01); *G16H 40/20* (2018.01)

(58) Field of Classification Search
CPC ....... G06F 19/327; G06K 9/32; G06T 7/0012; G06T 2207/10088; G06T 2207/10104
See application file for complete search history.

(56) References Cited

U.S. PATENT DOCUMENTS

| | | | | |
|---|---|---|---|---|
| 8,973,010 B2* | 3/2015 | Haas | ...................... | G06F 9/5066 718/105 |
| 2008/0141250 A1* | 6/2008 | Dorn | ...................... | G06F 9/5038 718/100 |
| 2010/0053178 A1* | 3/2010 | Lee | ......................... | G09G 5/006 345/522 |
| 2012/0291097 A1* | 11/2012 | Jones | ...................... | A61B 6/03 726/3 |

\* cited by examiner

*Primary Examiner* — Yon Couso

(57) ABSTRACT

A system that provides an improved way of scheduling a plurality of imaging tasks in a medical imaging system is disclosed. The system enables a user (i.e. a technician or medical expert) to group different imaging tasks and executes them simultaneously to significantly reduce scan time. These imaging tasks are of different types or are related to different imaging techniques. If different imaging tasks need to be performed substantially at the same location and have substantially same scan time then they can be scheduled simultaneously so that overall scan time can be reduced.

16 Claims, 4 Drawing Sheets

SYSTEM AND METHOD FOR SCHEDULING PLURALITY OF IMAGING TASKS IN A MEDICAL IMAGING SYSTEM

CROSS-REFERENCE TO RELATED APPLICATIONS

This application claims priority to India patent application number 1591/CHE/2015, filed on Mar. 27, 2015, the entirety of which is incorporated herein by reference.

BACKGROUND

The subject matter disclosed herein relates to a system for managing imaging tasks in a medical imaging system. More specifically it relates to a system and method for scheduling a plurality of imaging tasks in a medical imaging system for performing imaging on a subject.

Medical imaging systems with multiple imaging techniques combined in a single system are available for performing imaging on subjects. One of a kind of medical imaging system is PET-MR imaging system that allows user to simultaneously acquire PET and MR sequences leading to significant scan time reduction. The PET-MR and MR systems have user interface comprising of various user interface (UI) windows and controls. These UI windows and controls capture various kinds of patient prescription, image information, and user actions. The PET and MR imaging procedures or tasks may be performed at different imaging locations with respect to subject's body and their scan centers may be also different. In another scenario the imaging locations and the scan centers of different imaging tasks may be closer and thus these imaging tasks may be performed simultaneously. Present system enables these tasks such as MR and PET imaging tasks to be performed simultaneously. Currently the user reviews each and every imaging task and determines which of these imaging tasks can be grouped to be executed simultaneously. The grouping of the imaging tasks is performed manually by the user. For grouping the imaging tasks for example MR and PET imaging tasks, scan time needs to be manually calculated by the user which is time consuming. Once the scan time is calculated then the imaging tasks need to be made simultaneous manually. As manual grouping is performed it is prone to inaccuracy it also results in low user experience and throughput.

Accordingly, a need exists for an improved system for managing and scheduling imaging tasks.

SUMMARY

The object of the invention is to provide an improved system for scheduling a plurality of imaging tasks in a medical imaging system, which overcomes one or more drawbacks of the prior art. This is achieved by the system having the capability of as defined in the independent claim.

One advantage with the disclosed system is that it provides an improved way of scheduling a plurality of imaging tasks in a medical imaging system. The system enables a user (i.e. a technician or medical expert) to group different imaging tasks and executes them simultaneously to significantly reduce scan time. These imaging tasks are of different types or are related to different imaging techniques. If different imaging tasks need to be performed substantially at the same location and have substantially same scan time then they can be scheduled simultaneously so that overall scan time can be reduced.

In an embodiment a system for scheduling a plurality of imaging tasks in a medical imaging system is disclosed. The system includes an imaging task processor configured to analyze the plurality of imaging tasks, wherein the plurality of imaging tasks includes a plurality of first imaging tasks and a plurality of second imaging tasks. One or more first imaging tasks and one or more second imaging tasks are grouped. An imaging task processor is configured to execute one or more first imaging tasks and one or more second imaging tasks simultaneously for performing imaging.

In another embodiment a method of scheduling a plurality of imaging tasks in a medical imaging system is disclosed. The method includes analyzing a plurality of imaging tasks, wherein the plurality of imaging tasks includes a plurality of first imaging tasks and a plurality of second imaging tasks. One or more first imaging tasks and one or more second imaging tasks are grouped. Thereafter the one or more first imaging tasks and the one or more second imaging tasks are executed simultaneously for performing imaging.

A more complete understanding of the present invention, as well as further features and advantages thereof, will be obtained by reference to the following detailed description and drawings.

DETAILED DESCRIPTION

In the following detailed description, reference is made to the accompanying drawings that form a part hereof, and in which is shown by way of illustration specific embodiments that may be practiced. These embodiments are described in sufficient detail to enable those skilled in the art to practice the embodiments, and it is to be understood that other embodiments may be utilized and that logical, mechanical and other changes may be made without departing from the scope of the embodiments. The following detailed description is, therefore, not to be taken as limiting the scope of the invention.

As discussed in detail below, embodiments of a system for scheduling a plurality of imaging tasks in a medical imaging system is disclosed. The system includes an imaging task processor configured to analyze the plurality of imaging tasks, wherein the plurality of imaging tasks includes a plurality of first imaging tasks and a plurality of second imaging tasks. One or more first imaging tasks and one or more second imaging tasks are grouped. An imaging task processor is configured to execute one or more first imaging tasks and one or more second imaging tasks simultaneously for performing imaging.

In another embodiment a method of scheduling a plurality of imaging tasks in a medical imaging system is disclosed. The method includes analyzing a plurality of imaging tasks, wherein the plurality of imaging tasks includes a plurality of first imaging tasks and a plurality of second imaging tasks. One or more first imaging tasks and one or more second imaging tasks are grouped. Thereafter the one or more first imaging tasks and the one or more second imaging tasks are executed simultaneously for performing imaging.

Figure 1:
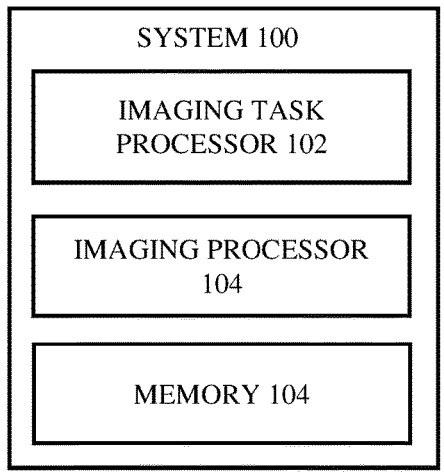
FIG. 1 is a schematic illustration of a system for scheduling a plurality of imaging tasks in a medical imaging system according to an embodiment.

FIG. 1 is a schematic illustration of a system 100 for scheduling a plurality of imaging tasks in a medical imaging system according to an embodiment. The medical imaging system may include, but not limited to a positron emission transmission (PET)-magnetic resonance (MR) imaging system, a positron emission transmission (PET)-computed tomography (CT) imaging system, and so on. The imaging tasks may be associated but not limited to PET, CT and MR imaging techniques. A user (i.e. a technician or a medical expert) may schedule different imaging tasks that need to be performed on subject's body. For instance PET and MR imaging tasks may be performed on the subject's body using a PET-MR imaging system. The PET and MR imaging tasks may be performed at the same location or approximately closer locations on the subject's body. Further scan time for the PET imaging task and the MR imaging task may be substantially same in some instances and in other instances execution time of the MR imaging task may be less than execution time of the PET imaging task. Execution time of an imaging task may be a time required for performing the imaging task completely. If these imaging tasks can be grouped together based on their imaging location and the execution time then the time required for imaging tasks can be reduced. The imaging location refers to location or portion of subject's body where the imaging needs to be performed.

The system 100 includes an imaging task processor 102 for analyzing the plurality of imaging tasks. The plurality of imaging tasks includes a plurality of first imaging tasks and a plurality of second imaging tasks. In an exemplary scenario a first imaging task may be associated with a PET imaging technique and a second imaging task may be associated with a MR imaging technique. Based on the analysis, the imaging task processor 102 groups one or more first imaging tasks and one or more second imaging tasks. In an embodiment the one or more first imaging tasks and the one or more second imaging tasks are grouped based on imaging locations of these tasks. The imaging task processor 102 determines an imaging location of a first imaging task and an imaging location of the second imaging task. If a first imaging task is performed in an imaging location similar or substantially similar to an imaging location where a second imaging task may be performed then these tasks may be grouped. The grouped first imaging tasks and the second imaging tasks are executed simultaneously for performing imaging on the subject's body.

In another embodiment the one or more first imaging tasks and the one or more second imaging tasks may be grouped based on execution time of these tasks. A first imaging task and a second imaging task may have different execution time. For example a first imaging task (i.e. a PET imaging task) may have higher execution time as compared to a second imaging task (i.e. a MR imaging task). Thus multiple MR imaging tasks may be grouped with the PET imaging task. A cumulative execution time of MR imaging tasks may be lesser than the execution time of the PET imaging task. In another instance cumulative execution time of MR imaging tasks may be equal to the execution time of the PET imaging task. Once the first imaging tasks and the second imaging tasks are grouped they are stored in a memory 104.

Figure 2:
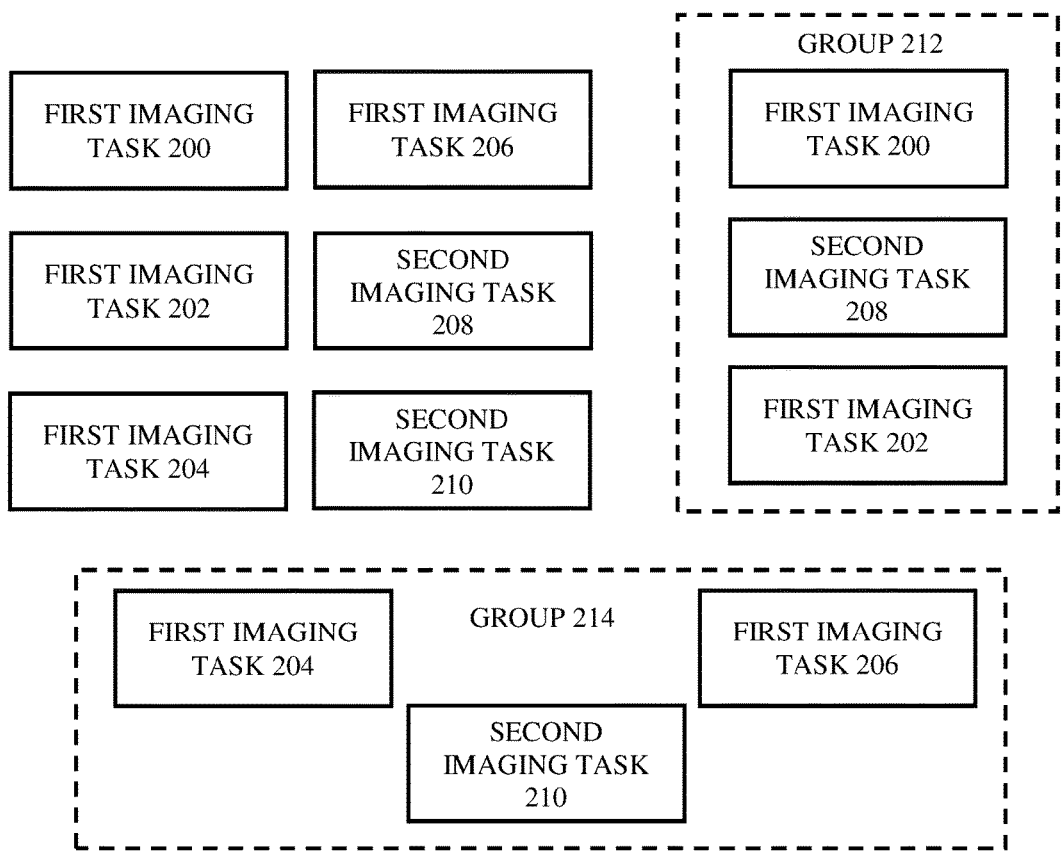
FIG. 2 is a schematic illustration of grouping of multiple first imaging tasks and multiple second imaging tasks according to an embodiment.

The technician or user can group multiple first imaging tasks and second imaging tasks in different groups according to an embodiment. FIG. 2 illustrates grouping of multiple first imaging tasks such as a first imaging task 200, a first imaging task 202, and a first imaging task 204; and multiple second imaging tasks such as a second imaging task 206, a second imaging task 208 and a second imaging task 210. The first imaging tasks 200, 202 and 204 may be associated with PET imaging technique. Further the second imaging tasks 206, 208 and 210 may be associated with MR imaging technique. The imaging task processor 102 analyzes these first imaging tasks and the second imaging tasks to determine their execution time and imaging locations. The imaging task processor 102 group the first imaging task 200, the second imaging task 208 and the first imaging task 202 in a group 212. The first imaging task 200 and the first imaging task 202 may need to be performed at an imaging location same as an imaging location of the second imaging task 208. This is further explained in conjunction with FIG. 3. Further cumulative execution time of the first imaging task 200 and the first imaging task 202 may be less than an execution time of the second imaging task 208. For example execution time of the first imaging task 200 may be 18 seconds, and the execution time of the first imaging task 202 may be 1 minute. The second imaging task 208 may have its associated execution time as 3 minutes. The cumulative execution time of the first imaging tasks 200 and 202 can be accommodated within the execution time of the second imaging task 208. Thus the first imaging tasks 200 and 202 can be executed simultaneously while executing the second imaging task 208. So when the second imaging task 208 is being performed the first imaging tasks 200 and 202 can be completed simultaneously thereby saving time.

The first imaging tasks 204 and 206 can also be grouped with the second imaging task 210 in a group 214. The execution time of the first imaging task 204 and the first imaging task 206 may be 1 minute and 1 minute respectively. Further the execution time of the second imaging task 210 may be 2 minutes. The first imaging tasks 204 and 206 can be accommodated along with the second imaging task 210. Accordingly the first imaging tasks 204 and 206 are grouped with the second imaging task 210 in grouped in group 214 and executed. The first imaging tasks 204 and 206 are performed are simultaneously when the second imaging task 210 is performed. As a result the first imaging tasks 204 and 206, and the second imaging task 210 can be completed within 2 minutes thereby saving the time.

Figure 3:
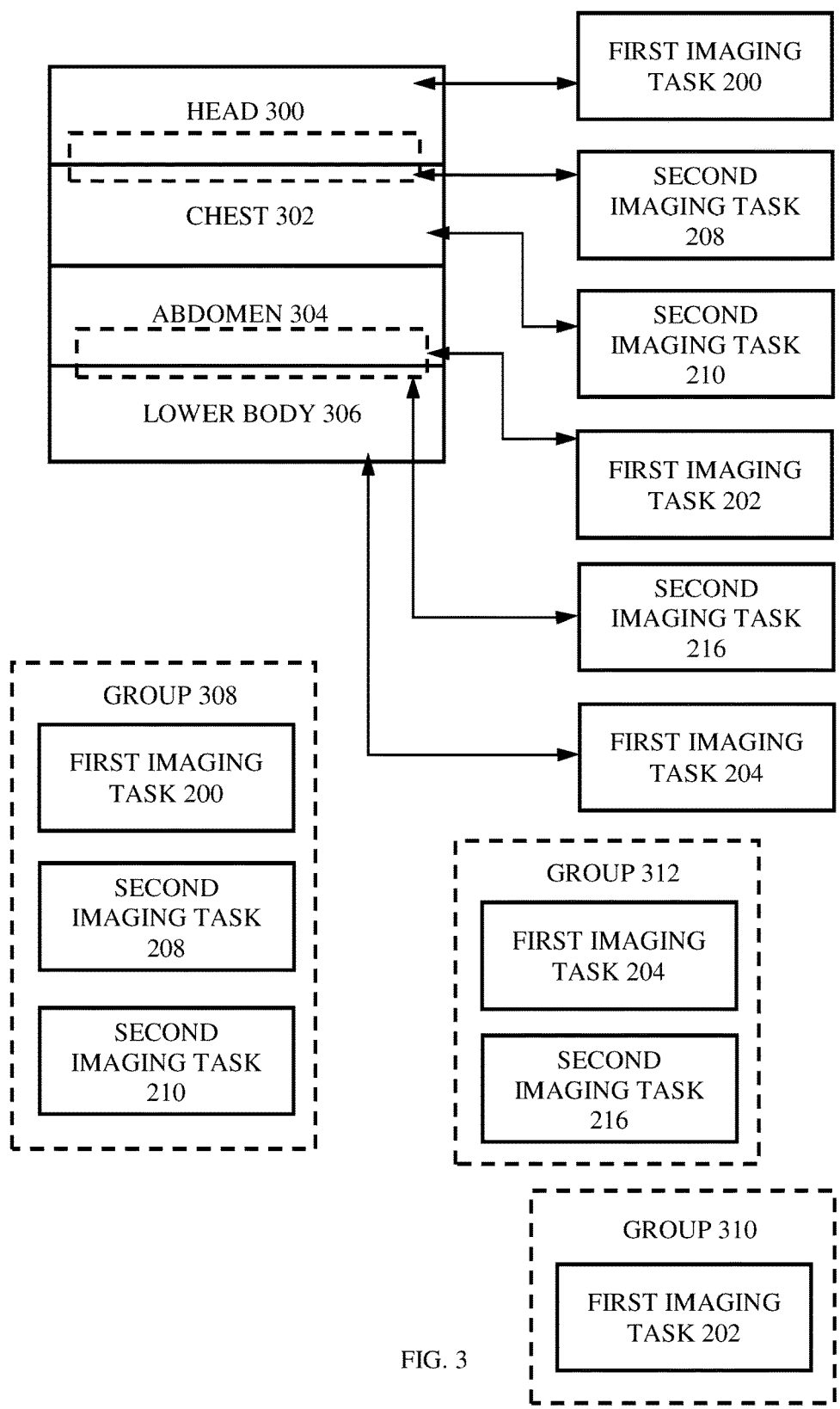
FIG. 3 is a schematic illustration of grouping of multiple first imaging tasks and multiple second imaging tasks based on scanning location with respect to a subject's body according to an exemplary embodiment.

FIG. 3 illustrates grouping the first imaging tasks and the second imaging tasks based on scanning location with respect to a subject's body according to an exemplary embodiment. The scanning locations as described herein is a mere exemplary scenario where the system 100 can operate to identify the first imaging tasks and the second imaging tasks that need to be arranged in different groups. The scanning locations include a head 300, a chest 302, an abdomen 304 and a lower body 306. The scanning locations as described herein are mere examples and there can be other scanning locations as part of the subject's body. The imaging task processor 102 analyzes these imaging tasks and identifies that the first imaging task 200 is associated with a scanning location i.e. the head 300, and the second imaging task 208 is associated with a scanning location which is between or overlapping with the head 300 and the chest 302. Moreover the second imaging task 210 is associated with a scanning location i.e. chest 302 which is closer to the scanning location of the second imaging task 208. In an embodiment an imaging centers within the scanning locations of the first imaging task 200, the second imaging task 208 and the second imaging task 210 are analyzed. In an instance execution time of the first imaging task 200 may be less than execution time of the second imaging task 208 or in another instance the execution time of the first imaging task 200 and the second imaging task 208 are substantially same. However the cumulative execution time of the second imaging tasks 208 and 210 may be substantially same or less than the execution time of the first imaging task 200. Accordingly these imaging tasks i.e. the first imaging task 200, the second imaging task 208 and the second imaging task 210 are grouped in a group 308. The imaging task processor 102 analyzes the first imaging task 202 and other imaging tasks which can be grouped. The imaging task processor 102 identifies that there are no imaging tasks having its scanning locations same or substantially same as the first imaging task 202. Thus the first imaging task 202 is included in a group 310. Explaining by way of an example, the first imaging task 200 may be a PET imaging task and the second imaging tasks 208 and 210 may be MR imaging tasks. The MR imaging tasks are non-simultaneous imaging tasks. The execution time of the PET imaging task is usually more than the execution time of the MR imaging tasks. So if the scanning location of the PET imaging task and the MR imaging tasks are same or substantially the same then it is checked whether the MR imaging tasks can be accommodated along with the PET imaging tasks based on their execution time. In another scenario, the scanning location and the execution time of the PET imaging task and the MR imaging tasks are analyzed simultaneously. However it may be noted that scanning location and the execution time of the PET imaging tasks and the MR imaging tasks can be analyzed in order or simultaneously in order to group these tasks without deviating from the scope of this disclosure. More specifically a cumulative execution time of the MR imaging tasks is substantially same or less than an execution time of the PET imaging task. For instance the second imaging tasks 208 and 210 may have execution time 2 minutes and 1 minute and the first imaging task 200 may have execution time 3.5 minutes. The cumulative execution time of the second imaging tasks 208 and 210 is 3 minutes which is less than the execution time of the first imaging task 200. The first imaging task 200, the second imaging task 208 and the second imaging task 210 are grouped in the group 308 to be performed simultaneously so that time required for completing these imaging tasks can be efficiently managed and higher throughput of the medical imaging system. In an embodiment a suggestion is provided to the user to group the first imaging task 200, the second imaging task 208 and the second imaging task 210 in the group 308. The suggestion is presented and based on the suggestion these imaging tasks can be grouped by the user. In another embodiment the first imaging task 200, the second imaging task 208 and the second imaging task 210 may be grouped automatically in the group 308. In yet another embodiment the first imaging task 200, the second imaging task 208 and the second imaging task 210 may not grouped to form any group however these imaging tasks may be performed simultaneously. The suggestion for simultaneously executing the first imaging task 200, the second imaging task 208 and the second imaging task 210 may be presented to the user. Upon receiving the user's confirmation these imaging tasks may be simultaneously executed.

Further another PET imaging task i.e. the first imaging task 202 may have an execution time of 4 minutes and as there are no MR imaging tasks that can be grouped along with the PET imaging task may performed alone at its time slot in the medical imaging system. A suggestion for grouping the first imaging task 202 may be presented to the user. Alternately the first imaging task 202 may be grouped automatically. The first imaging task 202 may not be grouped to form any group however the imaging task may be performed alone at its appropriate time slot in the medical imaging system.

The imaging task processor 102 analyzes other imaging tasks such as the second imaging task 216 and the first imaging task 204. The first imaging task 204 is associated with a scanning location overlapping the abdomen 304 and the lower body 306 of the subject. Whereas the second imaging task 216 needs to be performed at the lower body 306. As the scanning locations are overlapping then execution time of the first imaging task 204 and the second imaging task 216 are analyzed. The second imaging task 216 and the first imaging task 204 are grouped in a group 312. The user may be presented the suggestion for grouping the second imaging task 216 and the first imaging task 204. In another embodiment the second imaging task 216 and the first imaging task 204 are not grouped to form any group however these imaging tasks may be simultaneously executed in the medical imaging system. The suggestion for simultaneously executing the second imaging task 216 and the first imaging task 204 is presented to the user and these imaging tasks are simultaneously executed based on user's confirmation. As explained earlier the first imaging task 200, the first imaging task 202, the first imaging task 204, the second imaging task 206, a second imaging task 208, the second imaging task 210 and the second imaging task 216 may not be grouped to form any separate groups however these imaging tasks can be selected appropriately as explained in conjunction with FIGS. 2 and 3 to be performed simultaneously within the scope of this disclosure.

Figure 4:
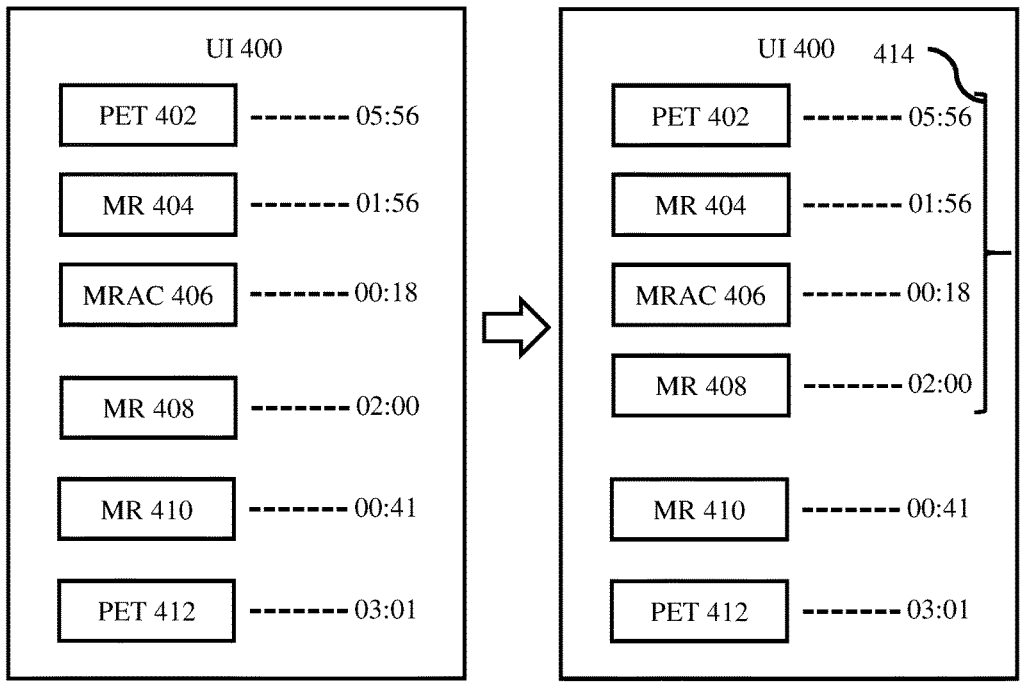
FIG. 4 is a schematic illustration of an exemplary user interface (UI) presented to the user that presents grouping of multiple imaging tasks according to an exemplary embodiment.

FIG. 4 illustrates an exemplary user interface (UI) 400 presented to the user that presents grouping of multiple imaging tasks according to an exemplary embodiment. The UI 400 is associated with a PET-MR imaging system. The UI 400 presents imaging tasks such as a PET 402, a MR 404, a magnetic resonance attenuation correction (MRAC) 406, a MR 408, a MR 410 and a PET 412. The PET 402 have an execution time of 5:56 minutes. As the PET 402 task has higher execution time, multiple imaging tasks can be made simultaneous to the PET 402 task for simultaneously execution. The system analyzes the imaging tasks i.e. the MR 404, the MRAC 406, the MR 408 and the MR 410 one by one to determine their scanning location and execution time. The MR 404 task, the MRAC 406 task and the MR 408 task have scanning locations same or substantially same as a scanning location of the PET 402 task. Further execution time of each of the MR 404 task, the MRAC 406 task and the MR 408 are also compared with the execution time of the PET 402 task.

The execution time associated with the MR 404 task, the MRAC 406 task and the MR 408 task are 1:56 minutes, 0.18 minutes and 2 minutes respectively. The cumulative execution time for these imaging tasks 4 minutes 14 seconds which is less than execution time of the PET 402. Thus the MR 404 task, the MRAC 406 task and the MR 408 task can be made simultaneous to the PET 402 task. In an embodiment the MR 404 task, the MRAC 406 task and the MR 408 task can be grouped with the PET 402 task as a group 414. These MR imaging tasks are executed simultaneously with the PET 402 task thereby improving the efficiency and throughput of the medical imaging system. Similarly other imaging tasks such as the MR 408, the MR 410 and the PET 412 tasks can be grouped or made simultaneous based on their scanning location and execution time.

Figure 5:
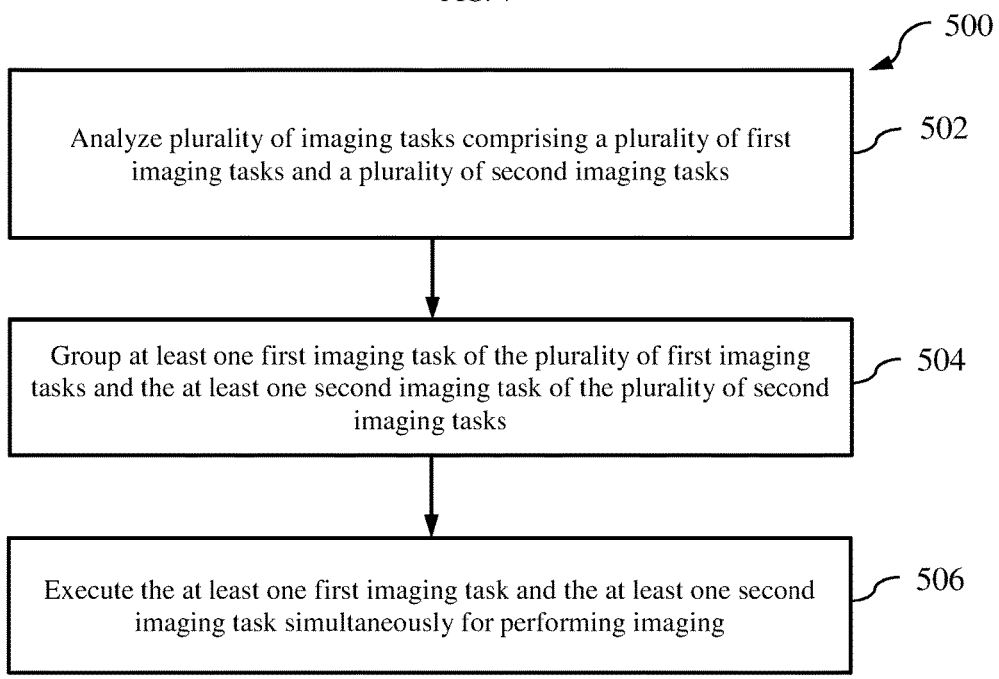
FIG. 5 is a flow diagram of a method of scheduling a plurality of imaging tasks in a medical imaging system according to an embodiment.

FIG. 5 illustrates a flow diagram of a method 500 of scheduling a plurality of imaging tasks in a medical imaging system according to an embodiment. At block 502 the plurality of imaging tasks are analyzed. The plurality of imaging tasks includes a plurality of first imaging tasks and a plurality of second imaging tasks. The first imaging tasks may be associated with a PET imaging technique and the second imaging tasks may be associated with a MR imaging task. Based on the analysis, one or more first imaging tasks and one or more second imaging tasks are grouped at block 504. The grouping is presented as a suggestion to the user. The user can confirm the grouping based on the suggestion. In an embodiment grouping of the first imaging tasks and the second imaging tasks may be imaginary however these imaging tasks may be made simultaneous for execution. Each imaging tasks such as the first imaging tasks and the second imaging tasks have associated execution time. The execution time refers to time required for executing an imaging task in the medical imaging system. Further these imaging tasks may be performed at an imaging location or scanning location associated with the subject's body. The imaging location and the execution time associated with the one or more first imaging tasks and the one or more second imaging tasks are analyzed. Based on the analysis the one or more first imaging tasks and the one or more second imaging tasks are executed simultaneously for performing imaging at block 506. The one or more second imaging tasks may have a cumulative execution time substantially equal to a cumulative execution time associated with the one or more first imaging tasks.

Figure 6:
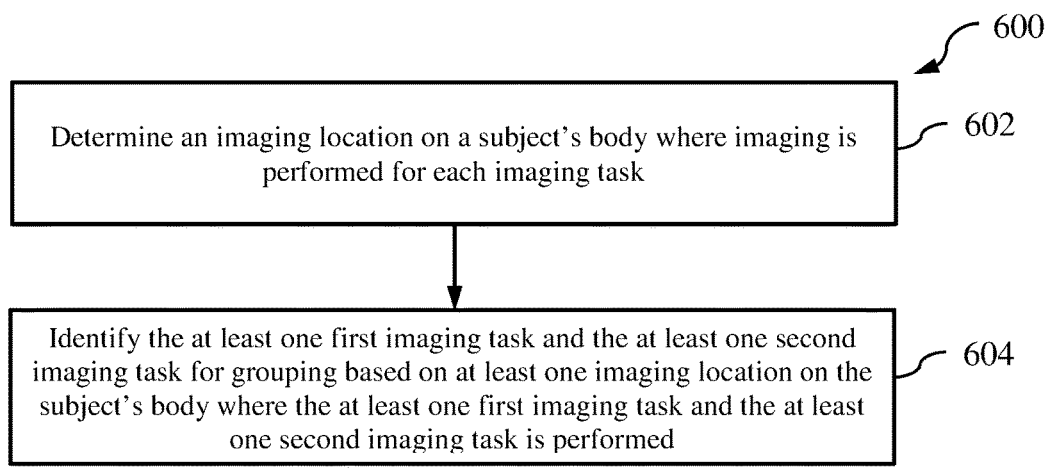
FIG. 6 illustrates a flow diagram of a method for grouping the one or more first imaging tasks and the one or more second imaging tasks based on an imaging location associated with each imaging task according to an embodiment.

FIG. 6 illustrates a flow diagram of a method 600 for grouping the one or more first imaging tasks and the one or more second imaging tasks based on an imaging location associated with each imaging task according to an embodiment. At block 602 an imaging location on a subject's body where imaging is performed is determined for each imaging task. Further it is identified whether the one or more first imaging tasks and the one or more second imaging tasks are grouped based on one or more imaging locations associated with subject's body where the one or more first imaging tasks and the one or more second imaging tasks are performed at block 604. Here one or more imaging location where the one or more first imaging task is performed is substantially near to one or more imaging locations where the one or more second imaging locations are performed.

Figure 7:
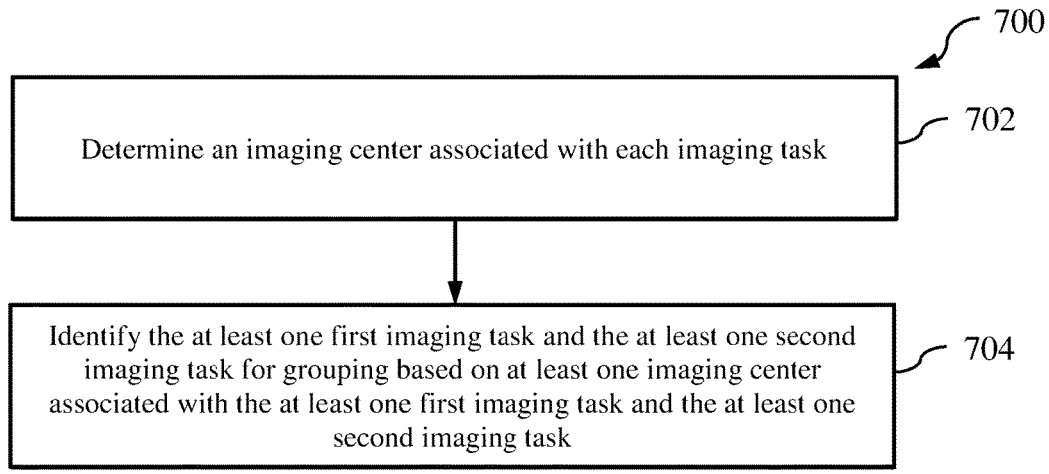
FIG. 7 illustrates a flow diagram of a method for grouping the one or more first imaging tasks and the one or more second imaging tasks based on an imaging center associated with each imaging task according to another embodiment.

FIG. 7 illustrates a flow diagram of a method 700 for grouping the one or more first imaging tasks and the one or more second imaging tasks based on an imaging center associated with each imaging task according to another embodiment. At block 702 an imaging center where imaging is performed for each imaging task is determined. Further it is identified whether the one or more first imaging tasks and the one or more second imaging tasks are grouped based on one or more imaging centers where the one or more first imaging tasks and the one or more second imaging tasks are performed at block 704. Here one or more imaging centers where the one or more first imaging task is performed are substantially near to one or more imaging centers where the one or more second imaging locations are performed.

From the foregoing, it will be appreciated that the above disclosed is a system for scheduling a plurality of imaging tasks in a medical imaging system. The system presents automatic suggestion for making the imaging tasks for example PET imaging tasks and MR imaging tasks, simultaneous to a user. The user can confirm these suggestions and different imaging tasks may be executed simultaneously. For instance one or more MR imaging tasks may be made simultaneous along with a PET imaging task thereby improving the throughput of the medical imaging system. Here non-simultaneous MR imaging tasks are made simultaneous with respect to a PET imaging task. Thus the system provides intelligent feedback or suggestions for making MR imaging tasks simultaneous with respect to a PET imaging task. Usually the PET imaging task has higher execution time and to make the system efficient non-simultaneous MR imaging tasks having cumulative execution time same or less than execution time of the PET imaging task are made simultaneous with respect to the PET imaging task.

This written description uses examples to disclose the invention, including the best mode, and also to enable any person skilled in the art to practice the invention, including making and using any computing system or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

I claim:

1. A system for automated simultaneous acquisition of PET and MR images in a PET-MR imaging system, the system comprising:
   a user interface coupled to the PET-MR imaging system for controlling operation of the PET-MR imaging system; and
   an imaging acquisition processor coupled to the PET-MR imaging system;
   wherein at least one PET imaging acquisition and at least one MR imaging acquisition is selectable from the user interface; and
   wherein the imaging acquisition processor determines an execution time and a location on a subject being imaged of the at least one PET imaging acquisition and an execution time and a location on the subject being imaged of the at least one MR imaging acquisition and provides selectable options on the user interface for performing at least one automated simultaneous PET and MR image acquisition.

2. The system of claim 1, wherein each of the at least one PET imaging acquisition and at least one MR imaging acquisition has a respective execution time for execution of each imaging acquisition.

3. The system of claim 2, wherein the imaging acquisition processor groups the imaging acquisitions based on the execution time of each of the at least one PET imaging acquisition and the execution time of each of the at least one MR imaging acquisition.

4. The system of claim 1, wherein the imaging acquisition processor provides selectable options on the user interface for grouping of the at least one PET imaging acquisition and the at least one MR imaging acquisition or grouping a combination of PET imaging acquisitions and MR imaging acquisitions to a user.

5. The system of claim 1, wherein the at least one PET imaging acquisition and the at least one MR imaging acquisition are different imaging techniques.

6. The system of claim 1, wherein the imaging acquisition processor
determines an imaging location associated with a subject's body for each PET imaging acquisition and each MR imaging acquisition; and
identifies the at least one PET imaging acquisition and the at least one MR imaging acquisition for grouping based on at least one imaging location associated with the subject's body where the at least one PET imaging acquisition and the at least one MR imaging acquisition are performed.

7. The system of claim 6, wherein the at least one imaging location associated with the subject's body where the at least one PET imaging acquisition is performed is different from the at least one imaging location associated with the subject's body where the at least one MR imaging acquisition is performed.

8. The system of claim 7, wherein the imaging acquisition processor
determines an imaging center associated with each PET imaging acquisition and each MR imaging acquisition; and
identifies the at least one PET imaging acquisition and the at least one MR imaging acquisition for grouping based on at least one imaging center where the at least one PET imaging acquisition and the at least one MR imaging acquisition are performed.

9. The system of claim 8, wherein the imaging center associated with at least one PET imaging acquisition is different from the imaging center associated with the at least one MR imaging acquisition.

10. A method for automated simultaneous acquisition of PET and MR images in a PET-MR imaging system, the method comprising:
selecting from a plurality of imaging acquisitions on a user interface coupled to the PET-MR imaging system, wherein the plurality of imaging acquisitions comprises a plurality of PET imaging acquisitions and a plurality of MR imaging acquisitions;
an imaging acquisition processor automatically grouping at least one PET imaging acquisition with at least one MR imaging acquisition, wherein the imaging acquisition processor is coupled to the PET-MR imaging system; and
the imaging acquisition processor executing the at least one PET imaging acquisition and the at least one MR imaging acquisition simultaneously for performing PET-MR imaging.

11. The method of claim 10, wherein each of the at least one PET imaging acquisition and at least one MR imaging acquisition has a respective execution time for execution of each imaging acquisition.

12. The method of claim 11, wherein grouping is performed based on the execution time of each of the at least one PET imaging acquisition and the execution time of each of the at least one MR imaging acquisition.

13. The method of claim 10 further comprising:
determining an imaging location on a subject's body for each PET imaging acquisition and each MR imaging acquisition; and
identifying the at least one PET imaging acquisition and the at least one MR imaging acquisition for grouping based on at least one imaging location on the subject's body where the at least one PET imaging acquisition and the at least one MR imaging acquisition are performed.

14. The method of claim 13, wherein the at least one imaging location on the subject's body where the at least one PET imaging acquisition is performed is different from the at least one imaging location on the subject's body where the at least one MR imaging acquisition is performed.

15. The method of claim 10 further comprising:
determining an imaging center associated with each PET imaging acquisition and each MR imaging acquisition; and
identifying the at least one PET imaging acquisition and the at least one MR imaging acquisition for grouping based on at least one imaging center associated with the at least PET imaging acquisition and the at least one MR imaging acquisition.

16. The method of claim 15, wherein the imaging center associated with the at least one PET imaging acquisition is different from the imaging center associated with the at least one MR imaging acquisition.

* * * * *